(12) United States Patent
White et al.

(10) Patent No.: US 11,433,198 B2
(45) Date of Patent: Sep. 6, 2022

(54) METHODS AND APPARATUS FOR FLOW THERAPY (71) Applicant: Fisher & Paykel Healthcare Limited, Auckland (NZ)

(72) Inventors: Craig Karl White, Auckland (NZ); Alicia Jerram Hunter Evans, Auckland (NZ); Callum James Thomas Spence, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 870 days.

(21) Appl. No.: 15/310,746

(22) PCT Filed: May 15, 2015

(86) PCT No.: PCT/NZ2015/050062
§ 371 (c)(1),
(2) Date: Nov. 11, 2016

(87) PCT Pub. No.: WO2015/174864
PCT Pub. Date: Nov. 19, 2015

(65) Prior Publication Data
US 2017/0087316 A1 Mar. 30, 2017

Related U.S. Application Data (60) Provisional application No. 62/046,000, filed on Sep. 4, 2014, provisional application No. 62/036,769, filed
(Continued)

(51) Int. Cl.
*A61M 16/00* (2006.01)
*A61M 16/10* (2006.01)
(Continued)

(52) U.S. Cl.
CPC .......... *A61M 16/0069* (2014.02); *A61B 5/01* (2013.01); *A61B 5/036* (2013.01); *A61B 5/08* (2013.01);
(Continued)

(58) Field of Classification Search
CPC ...... A61M 2205/3334; A61M 16/0069; A61M 16/0672; A61M 16/109; A61M 16/1095;
(Continued)

(56) References Cited

U.S. PATENT DOCUMENTS 5,271,389 A * 12/1993 Isaza ................... A61M 16/026
128/204.21
6,029,664 A 2/2000 Zdrojkowski et al.
(Continued)

FOREIGN PATENT DOCUMENTS

JP 2007530079 A * 7/2004 ............. A61B 5/411
WO WO 2005/011556 2/2005
(Continued)

OTHER PUBLICATIONS

Ohm's Law-Poiseuille's Law, Dec. 6, 2007 Hyperphysics, Georgia State University, http://hyperphysics.phy-astr.gsu.edu/hbase/electric/watcir2.html (Year: 2007).*
(Continued)

*Primary Examiner* — Margaret M Luarca
(74) *Attorney, Agent, or Firm* — Knobbe, Martens, Olson & Bear, LLP (57) ABSTRACT A method of estimating respiratory demand of a patient being administered flow therapy can include: administering a gas flow rate to the patient through both nostrils using a flow therapy apparatus with a patient interface for each nostril, measuring a parameter associated with that nostril, the parameter being one or more of: respiratory demand of that nostril, indicative of respiratory demand of that nostril,
(Continued)

or a parameter from which respiratory demand of that nostril can be derived, determining respiratory demand (or parameter indicative of respiratory demand) for the patient from the nostril parameter for each nostril.

19 Claims, 7 Drawing Sheets

Related U.S. Application Data on Aug. 13, 2014, provisional application No. 62/011,221, filed on Jun. 12, 2014, provisional application No. 61/994,374, filed on May 16, 2014.

(51) Int. Cl.
| | |
|---|---|
| A61M 16/16 | (2006.01) |
| A61B 5/01 | (2006.01) |
| A61B 5/03 | (2006.01) |
| A61B 5/087 | (2006.01) |
| A61B 5/00 | (2006.01) |
| A61M 16/06 | (2006.01) |
| A61B 5/08 | (2006.01) |

(52) U.S. Cl.
CPC ............ *A61B 5/087* (2013.01); *A61B 5/6819* (2013.01); *A61M 16/0057* (2013.01); *A61M 16/024* (2017.08); *A61M 16/0672* (2014.02); *A61M 16/109* (2014.02); *A61M 16/1095* (2014.02); *A61M 16/16* (2013.01); *A61M 16/161* (2014.02); *A61M 2016/0021* (2013.01); *A61M 2016/0027* (2013.01); *A61M 2016/0033* (2013.01); *A61M 2016/0039* (2013.01); *A61M 2016/0042* (2013.01); *A61M 2205/3334* (2013.01); *A61M 2205/3368* (2013.01); *A61M 2205/502* (2013.01)

(58) Field of Classification Search
CPC .............. A61M 16/161; A61M 16/024; A61M 2016/0015; A61M 2016/0018; A61M 2016/0021; A61M 2016/0027; A61M 2016/0033; A61M 2016/0036; A61M 16/0666; A61M 16/085; A61M 16/0858; A61B 5/036; A61B 5/037; A61B 5/038; A61B 5/08; A61B 5/087; A61B 5/6819
USPC .................................................. 128/204.23
See application file for complete search history.

(56) References Cited

U.S. PATENT DOCUMENTS

| | | | | |
|---|---|---|---|---|
| 8,631,799 | B2* | 1/2014 | Davenport | ........ A61M 16/0051 128/207.18 |
| 2004/0069304 | A1 | 4/2004 | Jam | |
| 2005/0121033 | A1* | 6/2005 | Starr | ................... A61M 16/024 128/204.18 |
| 2005/0257788 | A1 | 11/2005 | Aylsworth et al. | |
| 2006/0005842 | A1* | 1/2006 | Rashad | ............. A61M 16/0666 128/207.18 |
| 2006/0162727 | A1* | 7/2006 | Biondi | .................. A61M 16/00 128/204.21 |
| 2006/0174885 | A1* | 8/2006 | Aylsworth | ........ A61M 16/0069 128/206.11 |
| 2007/0113847 | A1* | 5/2007 | Acker | ................... A61M 16/00 128/204.18 |
| 2008/0142019 | A1* | 6/2008 | Lewis | ................. A61M 16/049 128/207.18 |
| 2009/0156952 | A1* | 6/2009 | Hunter | ................... A61M 15/02 600/538 |
| 2009/0253995 | A1* | 10/2009 | Lewis | .................... A61B 5/087 600/538 |
| 2011/0114098 | A1* | 5/2011 | McAuley | ............... A61M 16/06 128/207.18 |
| 2011/0214676 | A1* | 9/2011 | Allum | ............... A61M 16/0672 128/207.18 |
| 2013/0012828 | A1* | 1/2013 | Aylsworth | ............. A61B 5/085 600/538 |

FOREIGN PATENT DOCUMENTS

| | | |
|---|---|---|
| WO | WO 2010/076704 | 7/2010 |
| WO | WO 2014/140278 | 9/2014 |
| WO | WO 2014/196875 A1 | 12/2014 |
| WO | WO 2015/033288 | 3/2015 |
| WO | WO 2015/174864 | 11/2015 |

OTHER PUBLICATIONS

International Search Report and Written Opinion for PCT/NZ2015/050062 dated Aug. 7, 2015, in 18 pages.

Brighenti, C. et al., 'Effects of the Ventilator Patient Circuit on the Respiratory Parameter estimates: A Simulation Study', IFMBE Proceedings MEDICON, Modelling and Simulation of Physiological Systems, Jun. 12-15, 2001, Part II, pp. 915-918.

Lim, M. W. et al., 'Relationship of inspiratory and expiratory times to upper airway resistance during pulsatile needle cricothyrotomy ventilation with generic delivery circuit', British Journal of Anaesthesia, 2010, V104(1), pp. 98-107.

Meraz, E. et al., 'Modeling Human Respiratory Impedance in Hispanic Asthmatic Children', Proceedings of the 29th Annual International Conference of the IEEE EMBS, Aug. 23-26, 2007, pp. 4251-4254.

Nguyen, T-U. et al., 'A Study of IOS Data Using the aRIC+Ip Model of Respiratory Impedance', 31st Annual International Conference of the IEEE EMBS, Sep. 2-6, 2009, pp. 2875-2878.

* cited by examiner

2) $I_{P1} = \dfrac{V_M - V_{N1}}{R_{P1}}$

3) $I_{P2} = \dfrac{V_M - V_{N2}}{R_{P2}}$

4) $I_{L1} = \dfrac{V_{N1}}{R_{N1}}$

5) $I_{L2} = \dfrac{V_{N2}}{R_{N2}}$

METHODS AND APPARATUS FOR FLOW THERAPY

INCORPORATION BY REFERENCE TO ANY PRIORITY APPLICATIONS

This application is a national phase of PCT Application No. PCT/NZ2015/050062, filed May 15, 2015, which claims priority to U.S. Provisional Application Nos. 61/994,374, filed May 16, 2014; U.S. Provisional Application No. 62/011,221, filed Jun. 12, 2014; U.S. Provisional Application No. 62/036,769, filed Aug. 13, 2014; and U.S. Provisional Application No. 62/046,000, filed Sep. 4, 2014. Any and all applications for which a foreign or domestic priority claim is identified in the Application Data Sheet as filed with the present application are hereby incorporated by reference under 37 CFR 1.57.

FIELD OF THE INVENTION

The present invention relates to apparatus and/or methods for determining respiratory demand and/or controlling a breathing assistance apparatus based on the determination of respiratory demand.

SUMMARY OF THE INVENTION

It is object of the present invention to provide methods and/or apparatus for determining respiratory respiratory demand and/or to at least provide the public with a useful choice.

In accordance with at least one of the embodiments disclosed herein is a method of estimating respiratory demand of a patient being administered flow therapy comprising: administering a gas flow rate to the patient through both nostrils using a flow therapy apparatus with a patient interface, for each nostril, measuring a parameter associated with that nostril, the parameter being one or more of: respiratory demand of that nostril, indicative of respiratory demand of that nostril, or a parameter from which respiratory demand of that nostril can be derived, determining respiratory demand (or parameter indicative of respiratory demand) for the patient from the nostril parameter for each nostril.

In some configurations respiratory demand is: inspiratory demand, and/or expiratory demand.

In some configurations the parameter associated with each nostril is pressure of the nasal passage for that nostril and/or a pressure of a conduit leading to the nasal passage of that nostril.

In some configurations the respiratory demand for the patient is determined by: combining the pressure of the nasal passage for each nostril, and using a relationship to determine an offset flow rate or respiratory demand flow rate for the patient using the combined pressure, and/or using a relationship, determining and combining an offset flow rate or respiratory demand flow rate for each nostril using the nasal passage pressure for each nostril to provide an offset flow rate or respiratory demand flow rate for the patient.

In some configurations the relationship is one or more of: a look up table, mathematical relationship, and/or graph that correlates the offset flow rate and/or respiratory demand to nasal passage pressure.

In some configurations the mathematical relationship is:

$$Q_{offset} = SQR\left(\frac{ABS(P_T)}{R_{nasal}}\right)$$

where
$Q_{offset}$ is the nasal flow for the respective nasal passage at a point in time
$P_T$ is Terminal pressure (that is, patient pressure or nasal pressure) being a pressure in, at or near/proximate the outlet of the respective nasal prong and/or or in, at or near proximate the respective nasal passage of the patient at a point in time.
$R_{nasal}$ is the nasal resistance to flow of the respective nasal passage.
In some configurations: for non-laminar flow $$R_{nasal} = \frac{P_{trans} - P_{char}}{Q_{offset}^2}$$

wherein
$P_{trans}$ is the pressure at inspiration/expiration transition of breathing
$P_{char}$ is the system characteristic pressure at the point where pressure is being measured (which is zero or close to zero in the case of measuring pressure at the nasal passage/nasal prongs).
and for laminar flow $$R_{nasal} = \frac{P_{trans} - P_{char}}{Q_{offset}}$$

wherein $P_{char}=0$ if the parameter associated with each nostril is the pressure of the nasal passage for that nostril.

In some configurations the mathematical relationship (formed from an electrical analogy of the patient) is:

$$I = V/R$$

wherein
I is current in the electrical analogy and corresponds to offset flow
V is voltage in the electrical analogy and corresponds to Nasal pressure
R is resistance in the electrical analogy and corresponds to nasal resistance to flow.

In some configurations: the total gas flow rate required to be supplied, and/or the gas flow rate to be required through each nasal prong, to meet respiratory demand (overall and/or for each nasal passage), can be determined using one or more of the following equations:

$$I_M = I_{P1} + I_{P2}$$

$$I_{P1} = \frac{V_M - V_{N1}}{R_{P1}}$$

$$I_{P2} = \frac{V_M - V_{N2}}{R_{P2}}$$

$$I_{L1} = \frac{V_{N1}}{R_{N1}}$$

$$I_{L2} = \frac{V_{N2}}{R_{N2}}$$

$$I_{L1} = I_{P1} + I_{N1}$$

$$I_{L2} = I_{P2} + I_{N2}$$

$$f(I_{P1}) = AI_{P1}^2 + BI_{P1} = R_{P1}$$

$$R_{P2} = CI_{P2}^2 + DI_{P2}$$

-continued $$R_{N1} = EI_{L1}^2 + FI_{L1}$$

$$R_{N2} = GI_{L2}^2 + HI_{L2}$$

where (and with reference to FIG. 4):
$V_M$ is the voltage of the manifold, which corresponds to the pressure in the manifold or the system pressure ($P_{sys}$)
$V_{n1}$ and $V_{n2}$ are the nasal passage voltages for nasal passages 1 and 2, which correspond to the pressure of nasal passages 1 and 2.
$I_M$ is the manifold current, which corresponds to the flow rates for the manifold or the system flow rate.
$I_{n1}$ and $I_{n2}$ are the nasal passage current for nasal passage 1 and 2, which correspond to the respiratory demand flow rates for nasal passages 1 and 2.
$I_{P1}$ and $I_{P2}$ are the prong currents for prongs 1 and 2, which correspond to the flow rates for prongs 1 and 2.
$I_{L1}$ and $I_{L2}$ are the respective leakage currents, which correspond to the respective leakage (offset) flow rates.
$R_{P1}$ and $R_{P2}$ are the prong electrical resistances for prongs 1 and 2, which correspond to the flow rate resistances (resistances to flow) for prongs 1 and 2.
$R_{N1}$ and $R_{N2}$ are the respective leakage electrical resistances, which correspond to the respective leakage (offset) flow rate resistances (resistances to flow).

In some configurations the method further comprises displaying the determined respiratory demand or parameter indicative thereof.

In some configurations the method further comprises manually or automatically controlling flow therapy based on the determined respiratory demand or parameter indicative thereof.

In accordance with at least one of the embodiments disclosed herein is a flow therapy apparatus comprising: a flow generator, one or more sensors, and a controller configured to: control the flow generator to administer a gas flow rate to the patient through both nostrils, for each nostril, measure from the one or more sensors a parameter associated with that nostril, the parameter being one or more of: respiratory demand of that nostril, indicative of respiratory demand of that nostril, or a parameter from which respiratory demand of that nostril can be derived, determine respiratory demand (or parameter indicative of respiratory demand) for the patient from the nostril parameter for each nostril.

In some configurations respiratory demand is: inspiratory demand, and/or expiratory demand.

In some configurations the parameter associated with each nostril is pressure of the nasal passage for that nostril and/or a pressure of a conduit leading to the nasal passage of that nostril.

In some configurations the respiratory demand for the patient is determined by the controller: combining the pressure of the nasal passage for each nostril, and using a relationship to determine an offset flow rate or respiratory demand flow rate for the patient using the combined pressure, and/or using a relationship, determining and combining an offset flow rate or respiratory demand flow rate for each nostril using the nasal passage pressure for each nostril to provide an offset flow rate or respiratory demand flow rate for the patient.

In some configurations the relationship is one or more of: a look up table, mathematical relationship, and/or graph, that correlates the offset flow rate to nasal passage pressure.

In some configurations the mathematical relationship is:

$$Q_{offset} = SQR\left(\frac{ABS(P_T)}{R_{nasal}}\right)$$

where
$Q_{offset}$ is the nasal flow for the respective nasal passage at a point in time
$P_T$ is Terminal pressure (that is, patient pressure or nasal pressure) being a pressure in, at or near/proximate the outlet of the respective nasal prong and/or or in, at or near proximate the respective nasal passage of the patient at a point in time
$R_{nasal}$ is the nasal resistance to flow of the respective nasal passage.

In some configurations:
for non-laminar flow $$R_{nasal} = \frac{P_{trans} - P_{char}}{Q_{offset}^2}$$

where:
$P_{trans}$ is the pressure at inspiration/expiration transition of breathing
$P_{char}$ is the system characteristic pressure at the point where pressure is being measured (which is zero or close to zero in the case of measuring pressure at the nasal passage/nasal prongs).
and for laminar flow $$R_{nasal} = \frac{P_{trans} - P_{char}}{Q_{offset}}$$

wherein $P_{char}=0$ if the parameter associated with each nostril is the pressure of the nasal passage for that nostril.

In some configurations the mathematical relationship (formed from an electrical analogy of the patient) is:
$I=V/R$ wherein I is current in the electrical analogy and corresponds to offset flow
V is voltage in the electrical analogy and corresponds to Nasal pressure
R is resistance in the electrical analogy and corresponds to nasal resistance to flow.

In some configurations wherein: the total gas flow rate required to be supplied, and/or the gas flow rate to be required through each nasal prong, to meet respiratory demand (overall and/or for each nasal passage), can be determined by the controller using one or more of the following equations:

$$I_M = I_{P1} + I_{P2}$$

$$I_{P1} = \frac{V_M - V_{N1}}{R_{P1}}$$

$$I_{P2} = \frac{V_M - V_{N2}}{R_{P2}}$$

$$I_{L1} = \frac{V_{N1}}{R_{N1}}$$

$$I_{L2} = \frac{V_{N2}}{R_{N2}}$$

-continued $$I_{L1} = I_{P1} + I_{N1}$$

$$I_{L2} = I_{P2} + I_{N2}$$

$$f(I_{P1}) = AI_{P1}^2 + BI_{P1} = R_{P1}$$

$$R_{P2} = CI_{P2}^2 = DI_{P2}$$

$$R_{N1} = EI_{L1}^2 + FI_{L1}$$

$$R_{N2} = GI_{L2}^2 + HI_{L2}$$

where:
$V_M$ is the voltage of the manifold, which corresponds to the pressure in the manifold or the system pressure ($P_{sys}$)
$V_{n1}$ and $V_{n2}$ are the nasal passage voltages for nasal passages 1 and 2, which correspond to the pressure of nasal passages 1 and 2.
$I_M$ is the manifold current, which corresponds to the flow rates for the manifold or the system flow rate.
$I_{n1}$ and $I_{n2}$ are the nasal passage current for nasal passage 1 and 2, which correspond to the respiratory demand flow rates for nasal passages 1 and 2.
$I_{P1}$ and $I_{P2}$ are the prong currents for prongs 1 and 2, which correspond to the flow rates for prongs 1 and 2.
$I_{L1}$ and $I_{L2}$ are the respective leakage currents, which correspond to the respective leakage (offset) flow rates.
$R_{P1}$ and $R_{P2}$ are the prong electrical resistances for prongs 1 and 2, which correspond to the flow rate resistances (resistances to flow) for prongs 1 and 2.
$R_{N1}$ and $R_{N2}$ are the respective leakage electrical resistances, which correspond to the respective leakage (offset) flow rate resistances (resistances to flow).

In some configurations the method further comprises the controller being configured to display the determined respiratory demand or parameter indicative thereof.

In some configurations the method further comprises the controller controlling flow therapy based on the determined respiratory demand or parameter indicative thereof.

In accordance with at least one of the embodiments disclosed herein is a flow therapy apparatus comprising: a flow generator, two sensors, each sensor for measuring a nasal parameter of a respective nasal passage, and a controller configured to: control the flow generator to administer a gas flow rate to the patient through both nasal passages, determine respiratory demand (or parameter indicative of respiratory demand) for a patient from a nasal parameters measured by each sensor for each respective nasal passage of the patient.

In some configurations each sensor is a pressure sensor and/or the nasal parameter is pressure, each sensor is a temperature sensor and/or the nasal parameter is temperature, and/or each sensor is a flow sensor and/or the nasal parameter is flow rate.

In some configurations the controller determines respiratory demand by: combining the nasal parameters and determining a respiratory demand for the patient, determining the maximum, minimum, average or other representative value of the nasal parameters and determining a respiratory demand for the patient, using each nasal parameter, determining and combining a respiratory demand or parameter indicative thereof for each nasal passage to determine a respiratory demand for the patient, using each nasal parameter, determining a respiratory demand or parameter indicative thereof for each nasal passage and determining the maximum, minimum, average or other representative value of the respiratory demand or parameter indicative thereof for each nasal passage to determine a respiratory demand for the patient.

In some configurations a high flow therapy can be a therapy that provides gas flow of one of: over 4 litres/minute, over 15 litres/minute, over 30 litres/minute In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

The term "comprising" as used in this specification means "consisting at least in part of". When interpreting each statement in this specification that includes the term "comprising", features other than that or those prefaced by the term may also be present. Related terms such as "comprise" and "comprises" are to be interpreted in the same manner.

This invention may also be said broadly to consist in the parts, elements and features referred to or indicated in the specification of the application, individually or collectively, and any or all combinations of any two or more said parts, elements or features, and where specific integers are mentioned herein which have known equivalents in the art to which this invention relates, such known equivalents are deemed to be incorporated herein as if individually set forth.

The invention consists in the foregoing and also envisages constructions of which the following gives examples only.

BRIEF DESCRIPTION OF THE DRAWINGS

Preferred embodiments of the invention will be described by way of example only and with reference to the drawings, in which.

DETAILED DESCRIPTION OF PREFERRED EMBODIMENTS

Overview

Flow therapy assists breathing through the provision of (preferably humidified) gas flows to a patient. Although flows of gas delivered via a patient interface exist in the prior art, an aspect of at least one of the embodiments disclosed herein includes the realisation that there are problems with the implementation and use of these high flow systems in the prior art. Prior art high flow therapy may not meet the respiratory demand (e.g. inspiratory demand or expiratory demand) of a patient. Inspiratory demand as herein described may refer to the amount of gas a patient may require during inspiration.

As an example, prior art systems may not measure or calculate this inspiratory demand, or may not determine inspiratory demand for individual patients. Thus the flow rate delivered to patients may not reflect their specific respiratory condition or individual demand, which may provide inadequate respiratory support and/or may compromise the effectiveness of the therapy. Flows delivered to a patient that are below their inspiratory demand may cause entrainment of room air during inspiration as the patient may require more gas to meet their inspiratory demand. Entrainment of room air may dilute the humidity, temperature, oxygen concentration, or other gases mixed into the delivered gas to the patient compromising the treatment and preventing effective control of the therapy. Flows delivered to a patient that are above inspiratory demand may cause undesired physiological outcomes, discomfort to the patient and may be associated with excess noise generation. Currently clinicians (e.g. doctors, nurses or other healthcare professionals) may be unsure as to the specific inspiratory demand of their patients, thus to prescribe a flow rate may be difficult and may not reflect the flow rate that best meets their patients' needs.

Embodiments described herein relate to apparatus and/or methods for determining respiratory demand (or parameters indicative of respiratory demand or from which respiratory demand can be determined) and/or controlling a flow therapy apparatus to provide flow therapy based on a determined respiratory demand.

Respiratory demand is a general term covering inspiratory demand and expiratory demand, either separately or together. Inspiratory/expiratory demand relates to the required gas flow rate (either inspiratory flow rate or respiratory flow rate as appropriate) "demanded" by the patient at any particular point in the breathing cycle. Peak inspiratory/expiratory demand relates to the required gas flow rate demanded at peak inspiration/expiration. For example, inspiratory demand (also termed "instantaneous inspiratory demand") is the gas flow rate that is needs to be delivered to/received by the patient at their nose (at a particular point in the breath cycle) to ensure there is no or minimal entrainment of gas flow into the nose from ambient at that point in the breath cycle. That is, the delivered/received gas flow rate is the same or more than the patient requires, thus preventing any shortfall that needs to be received from ambient. Peak inspiratory demand is the special case at the peak of patient inspiration (that is, when they have the highest inspiration gas flow rate).

It has been determined that while there is an overall/total respiratory demand that a patient requires during respiration through their nose via a nasal patient interface (e.g. a nasal cannula) during flow therapy, the respiratory demand of each nasal passage (also termed nostril or nare) may differ. This is because the nasal cycle is a continuous cycle of alternating nostrils partially closing and opening typically over a 45 minute to 6 hour period. The nasal cycle is thought to be a natural mechanism for each nostril alternatively working to condition (warm, filter, humidify) inspired air and followed by a period of rest. The asymmetry in nasal resistance due to the nasal cycle causes asymmetry in flow through each nostril. The proportion of the total inspiratory and/or expiratory flow through each nostril can therefore differ significantly. Inevitable inter-personal nostril geometry variation and breathing device interface placement will also compound to bias flow through one or the other nostril.

The respiratory demand of each nostril combines to provide the overall respiratory demand when breathing through the nose (that is, through both nasal passages) during flow therapy.

The embodiments described herein determine the overall/total respiratory demand of a patient (through the nose) during flow therapy based on parameters relating to the respiratory demand of each nasal passage of the patient during flow therapy.

In other embodiments, apparatus and methods are disclosed that may calculate or measure the expiratory flow rate of a patient. This information can be provided to a clinician and used by the clinician and/or by the apparatus to provide improved high flow therapy and/or other therapies.

A general description of a flow therapy apparatus (typically a high flow therapy apparatus) will be provided, and particular embodiments of the apparatus and its use will then be described. In general terms, the method and apparatus of the present specification utilise system pressure (being a pressure at some point in the high flow therapy apparatus) to determine respiratory flow rate. Possible embodiments comprise determining inspiratory flow rate (including peak inspiratory demand, instantaneous inspiratory demand), and determining the pressure in the manifold/cannula of the patient interface, as described below. These are non-limiting examples. Possible embodiments comprise determining expiratory flow rate (such as peak and/or instantaneous expiratory flow rate).

Flow Therapy Apparatus

Figure 1:
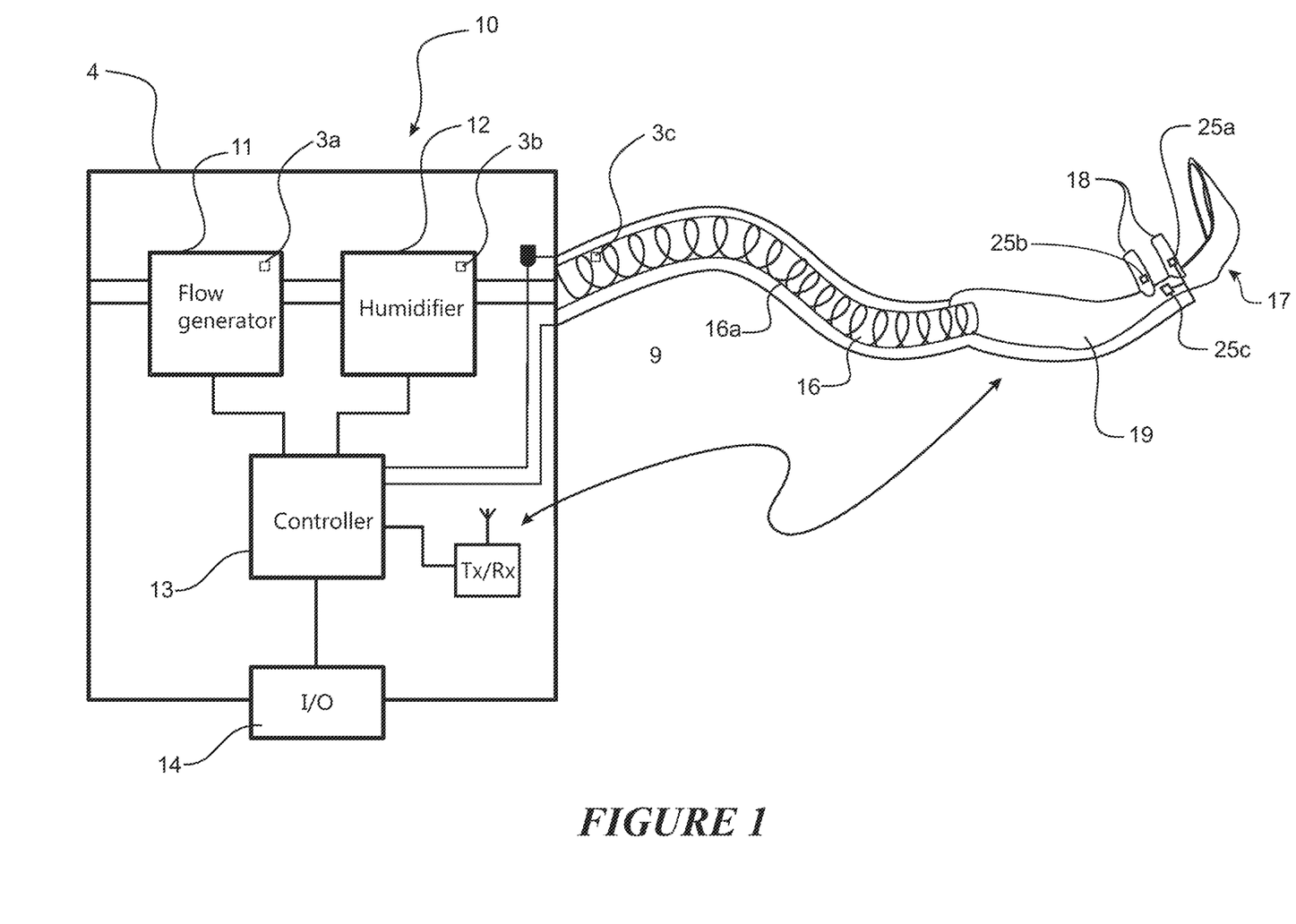
FIG. 1 illustrates a (e.g. high) flow therapy apparatus adapted to provide or assist to provide high flow therapy that meets respiratory demand of a patient.

A flow therapy apparatus 10 (breathing assistance apparatus) is shown in FIG. 1. It comprises a housing 4 that contains a flow generator 11, humidifier 12, controller 13 and user I/O interface 14 (comprising, for example, a display and input devices such as buttons or the like). The controller 13 is programmed to control the components of the apparatus, including: operating the flow generator 11 to create a flow of gas (gas flow) for delivery to a patient, operating the humidifier 12 to humidify and/or heat the generated gas flow, adjust the flow rate of other introduced gases, e.g. oxygen, receive user input from the user interface 14 for reconfiguration and/or user-defined operation of the apparatus 10, output information (for example on the display) to the user. It also receives input from sensors and is configured to use that input to determine respiratory demand and/or display respiratory demand as described below. The user could be a patient, healthcare professional or anyone else interested in using the apparatus.

A patient breathing conduit 16 is coupled to a gas flow output in the housing 4 of the high flow therapy apparatus 10, and is coupled to a patient interface, such as a nasal cannula 17 with a manifold 19 and nasal prongs 18. The humidified gas flow that is generated by the high flow therapy apparatus is delivered to the patient via the patient conduit 16 through the cannula 17. The patient conduit 16a can have a heater wire to heat gas flow passing through to the patient, under control of the controller 13. The patient conduit 16 and/or patient interface can be considered part of the high flow therapy apparatus 10, or alternatively peripheral to it. Use of the term "(high) flow therapy apparatus" can be utilised for either alternative. High flow therapy typically (although not exclusively) involves delivering flow rates of anything above 4 litres/min, or alternatively anything above 15 litres/min or alternatively anything above 30 litres/min to the patient to assist with breathing. The high flow therapy can also provide humidity. The apparatus might also comprise an inlet for a supplementary gas (such as oxygen or other suitable supplementary gas) that can be mixed with air to provide a mixed gas flow to the patient. Alternatively, pure gas (such as oxygen) could be provided instead of air.

General operation of a flow therapy breathing apparatus 10 will be known to those skilled in the art, and need not be described in detail here. However, in general terms the controller 13: controls the flow generator 11 to generate a gas flow of the desired flow rate (generated gas flow), and controls the humidifier 12 to humidify the gas flow and/or heat it. The gas flow is directed out through the patient conduit 16 and cannula 17 to the patient. The controller 13 can also control heating elements 16a in the humidifier and/or patient conduit to heat the gas to a desired temperature (also termed "target temperature" or "set point") that achieves the required level of therapy and/or comfort for the patient. The controller 13 can be programmed with or determine a suitable target temperature.

Operation sensors, e.g. 25a, 25b, 25c, 3a, 3b, 3c such as flow, temperature, humidity, gas concentration and/or pressure sensors can be placed in various locations in the flow therapy apparatus and/or the breathing conduit and/or cannula. Output from the sensors can be received by the controller 13, to assist it to operate the flow therapy apparatus in a manner that provides optimal therapy, including (although not limited to) meeting respiratory demand.

Figure 2:
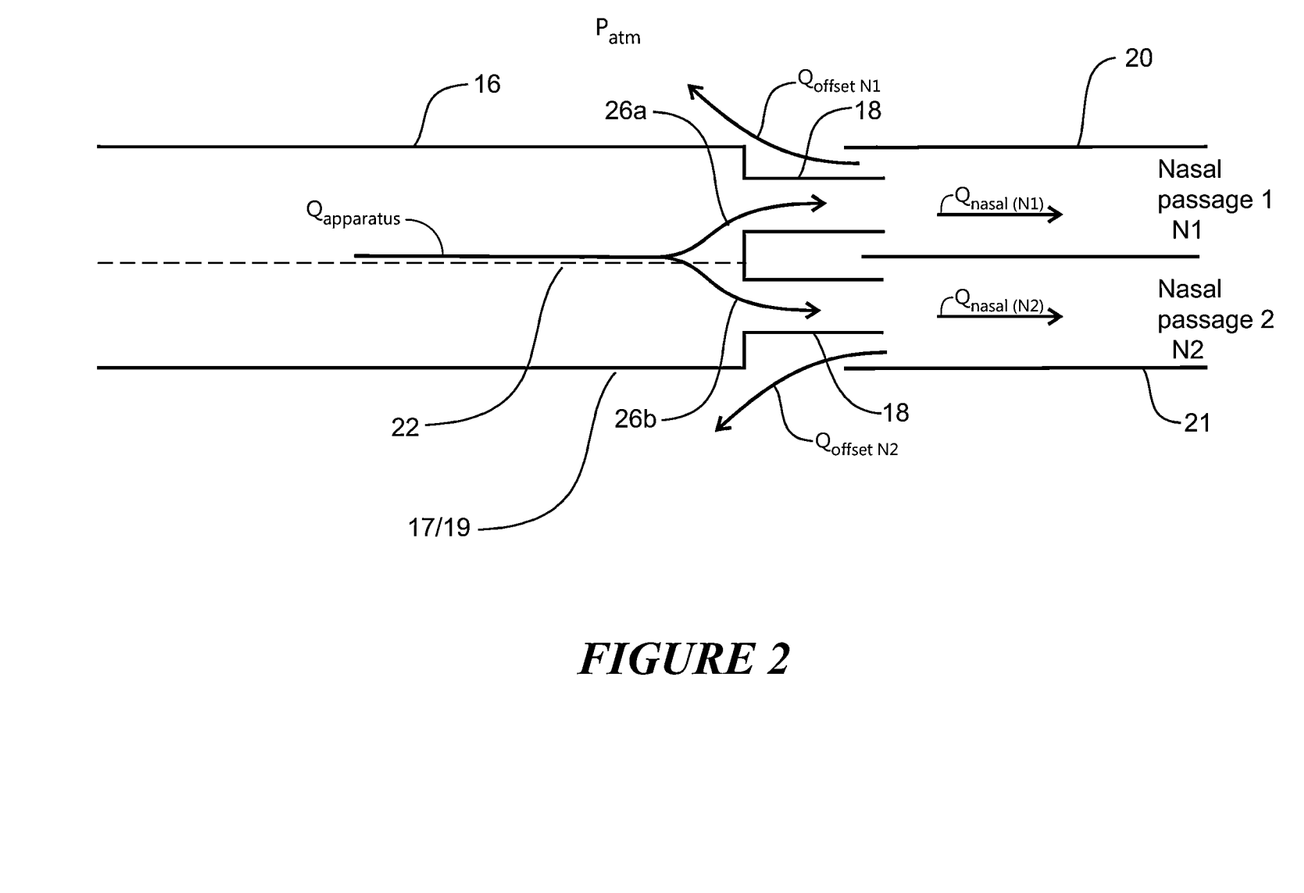
FIG. 2 illustrates in schematic form of the delivery conduit, nasal interface and nasal passages of the patient.

FIG. 2 shows schematically the patient/delivery conduit 16 and nasal cannula 17 of the breathing assistance apparatus and its position in relation to the nasal passages 20, 21 of the patient, along with the related breathing parameters. The delivery conduit 16 is connected to a nasal cannula with two nasal prongs 18, each of which sits within a respective nasal passage 20, 21 of the patient. There is a flow rate $Q_{apparatus}$ through the delivery conduit 16 which then splits into separate gas flows (with associated gas flow rates) 26a, 26b through the nasal prongs 18 and $Q_{nasal(N1)}$, $Q_{nasal(N2)}$ into the nasal passages. These flow rates could be in any direction. There is also an offset flow rate ($Q_{offsetN1, N2}$) for each nasal passage, being the flow rate of gas between the nasal passage and atmosphere. The offset flow indicates how much the incoming flow rate through the delivery conduit differs from the inspiratory or expiratory demand flow rate $Q_{nasal}$. There is a pressure point at each point throughout the delivery conduit 16, nasal cannula 17, nasal prongs 18 (each termed a "system pressure" $P_{system}$) and a pressure at the outlet of each nasal prong $P_{T(N1)}$, $P_{T(N2)}$ and at the inlet to each nasal passage 20, 21. There is also an atmospheric pressure $P_{atm}$. The delivery conduit, nasal cannula and nasal passages all have an associated resistance to flow parameter also, which in the case of the nasal passages is $R_{nasal(N1)}$, $R_{nasal(N2)}$. The nasal passages, nasal cannula, nasal prongs and/or delivery conduit can also have an associated temperature parameter, and/or other parameter indicated of respiratory demand $Q_{nasal}$, or form which respiratory demand can be derived.

It should be noted that while FIG. 2 shows schematically a single lumen delivery conduit, there could be a dual lumen delivery conduit, or dual single lumen delivery conduits, one for delivering gas flow to a respective nasal passage 20, 21 via an associated nasal prong 18. The dotted line 22 schematically indicates the possible dual lumen/dual conduit arrangement. In this case, the flow, pressure, temperature or any other parameter described could be measured independently in each of the delivery conduits, each one parameter relating to the associated nasal passage.

When determining respiratory demand of the patient (that is the overall/total respiratory demand through the nose during flow therapy), the embodiments described herein determine the respiratory demand (that is, the required respiratory or expiratory flow rate at any particular time) for each nasal passage using one or more parameters associated with each nasal passage, or they determine a parameter of each nasal passage, combine those parameters, and used that to determine the respiratory demand of the patient. Sensors e.g. 25a, 25b, 25c, 3c are placed to measure the desired parameters, which are then fed to the controller 13 of the apparatus which can then determine the respiratory demand or some parameter indicative of respiratory demand based on the combination of the parameters associated with each nasal passage. For example, but not limiting, the parameter could be the pressure in each nasal passage, from which the offset flow for each nasal passage can be determined, or the parameter could be offset flow itself. Another parameter associated with each nasal passage that could be used as temperature. The pressure, temperature or offset flow for each nasal passage can then be combined to indicate whether the overall respiratory demand is being met or not, and/or what that respiratory demand is.

In general terms, the apparatus and/or method are configured to determine the parameter associated with each nasal passage ("nasal parameter", such as flow, pressure or temperature), and from that determine the overall respiratory demand. This may be achieved by determining the respiratory demand (or parameter indicative thereof) for each nasal passage first, and combining them to find the overall respiratory demand (or parameter indicative thereof), or by finding the overall respiratory demand (or parameter indicative thereof) directly from a combination of the nasal parameters, or by any other suitable process. Alternatively, where two nasal parameters are obtained, rather than combining them, the maximum, minimum, average or some other value representative of the two nasal parameters is used to determine overall respiratory demand. Alternatively, where respiratory demand (or parameter indicative thereof) for each nasal passage is determined from the nasal parameters, rather than combining the two respiratory demands, the maximum, minimum, average or some other value representative of the two respiratory demands is used to determine overall respiratory demand. The term "combining" used in relation to nasal parameters, offset flows and/or respiratory demands can mean any of adding, subtracting, those parameters and/or taking the maximum, minimum, average or some other representative value of those parameters.

Figure 3:
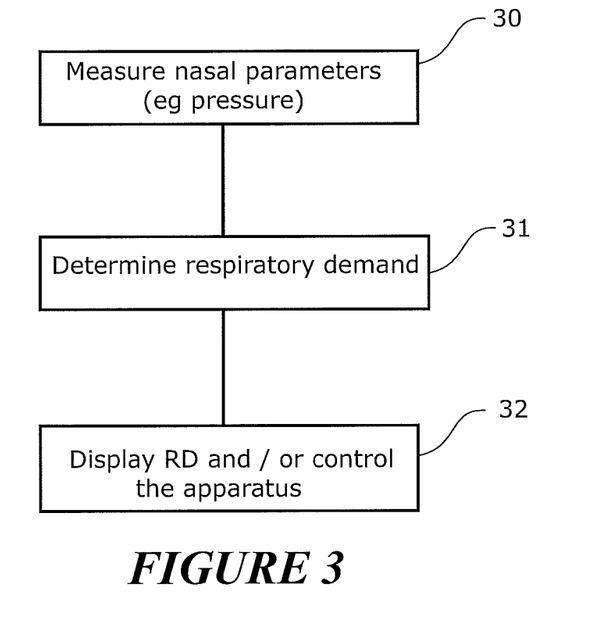
FIG. 3 shows a flow diagram of a method for determining respiratory demand in accordance with the first exemplary embodiment.

First Exemplary Embodiment for Determining Respiratory Demand from Nasal Pressure and Nasal Resistance to Flow A first exemplary embodiment will now be described with reference to FIG. 2 and the flow chart of FIG. 3. In this embodiment, there are pressure sensors 25a, 25b at, in or near/proximate each nasal prong or in, at or near/proximate each nare of the patient. Each sensor measures a pressure parameter being a nasal pressure ("nasal parameter") of the respective nasal passage, step 30. The nasal pressure can also be termed "patient pressure" or "terminal pressure" The controller 13 receives the pressure measurement from each sensor and is configured to determine an indication of respiratory demand, a parameter indicative of respiratory demand and/or whether respiratory demand is met from the nasal pressure parameters, step 31, in accordance with the apparatus and methods described in priority applications U.S. 62/036,769, U.S. 62/046,000 and PCT application published as WO2015/033288. The respiratory demand (or indicative parameter) can be displayed, and/or the apparatus can be manually or automatically controlled based on respiratory demand (or indicative parameter).

Figure 3A:
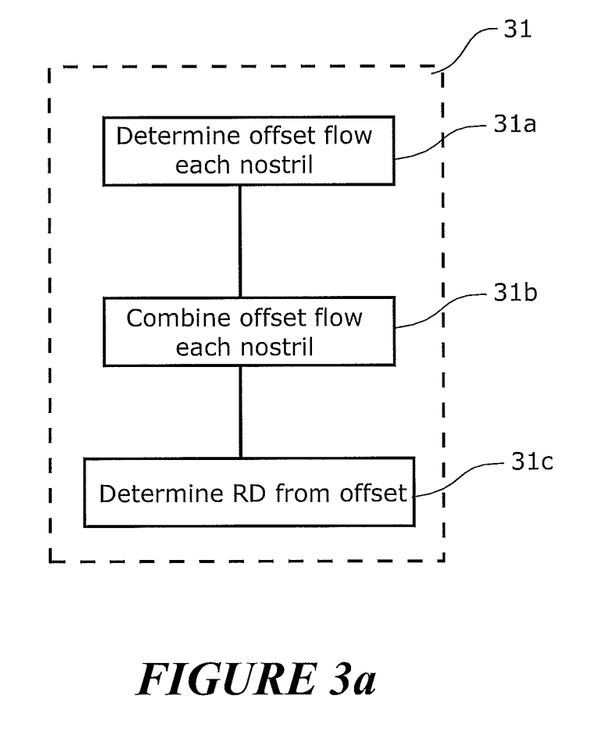
FIG. 3a shows further detail of the flow diagram of FIG. 3.

More particularly, referring to FIG. 3a (and with reference to an example of determining (instantaneous) inspiratory demand), the offset flow for each nasal passage 20, 21 is determined using each nasal pressure $P_{T(N1)}$, $P_{T(N2)}$ and also a nasal resistance to flow $R_{nasal(N1)}$, $R_{nasal(N2)}$ for each nasal passage, step 31a. Then the offset flow ($Q_{offsetN1}$, $Q_{offsetN2}$) for each nostril is combined to provide an overall offset flow, step 31b. From this the overall inspiratory demand can be determined, step 31c, (by adding or subtracting the offset flow from the flow rate 26a, 26b through the cannula). Also, or alternatively, the controller 13 or user can automatically/manually modify the flow rate 26a, 26b through the cannula by the value of the offset such that it meets inspiratory demand, step 32. These values can all be displayed and any control can be done manually or automatically, step 32. Whether inspiratory demand is being met, exceeded or not met can also be displayed, step 32. Alternatively, rather than combining flows, the maximum, minimum, average or some other representative value of the two flows is used to determine respiratory demand.

The offset flow for each nasal passage is calculated from the nasal pressure parameter and the nasal resistance to flow for each nostril using the following equation (1):

$$Q_{offset} = SQR\left(\frac{ABS(P_T)}{R_{nasal}}\right)$$

Where $Q_{offset}$ is the nasal flow for the respective nasal passage at a point in time $P_T$ is Terminal pressure (that is, patient pressure or nasal pressure) being a pressure in, at or near/proximate the outlet of the respective nasal prong and/or or in, at or near proximate the respective nasal passage of the patient at a point in time $R_{nasal}$ is the nasal resistance to flow of the respective nasal passage.

$P_T$ could be positive or negative during inspiration. (It will always be positive during expiration.) So the numerator for $Q_{offset}$ has an absolute sign to avoid having a square root of a negative number.

The nasal resistance to flow for each nostril is found using the following equation (2) for non-laminar flow:

$$R_{nasal} = \frac{P_{trans} - P_{char}}{Q_{offset}^2}$$

Where:

$P_{trans}$ is the pressure at inspiration/expiration transition of breathing $P_{char}$ is the system characteristic pressure at the point where pressure is being measured (which is zero or close to zero in the case of measuring pressure at the nasal passage/nasal prongs).

In the case of laminar flow, the following equation 93) is used.

$$R_{nasal} = \frac{P_{trans} - P_{char}}{Q_{offset}}$$

The method for determining offset flow from terminal pressure and a nasal resistance to flow is described further in priority applications U.S. 62/036,769, U.S. 62/046,000 and PCT application published as WO2015/033288. Other variations can be used as described also.

Furthermore, the approach can be modified to determine peak inspiratory demand, (instantaneous) expiratory demand and/or peak expiratory demand as described in priority applications U.S. 62/036,769, U.S. 62/046,000 and PCT application published as WO2015/033288.

In a variation, rather than determining the offset flow for each nasal passage, then combining them to determine the overall offset flow/respiratory demand, each nasal pressure might be combined (or a maximum, minimum, average or other representative value obtained), and the overall offset flow/respiratory demand found directly from that.

Also, more generally in a variation of the first exemplary embodiment, the pressure parameter for each nasal passage might not be measured at the nasal passage itself, but rather at some point in the system ($P_{system}$) prior to the nasal passage, like in the nasal prong, or other conduit dedicated to the nasal passage in question using a pressure sensor positioned (e.g. 3c, 25c) as required. This pressure is a system pressure. In this case a characteristic pressure of the system between the pressure measurement point and the nasal passage is used to determine the terminal pressure from the system pressure. In this case, the controller is configured to determine terminal pressure from the measured system pressure in accordance with the following equation (4).

$$P_T = P_{sys} - P_{char}$$

where $P_T$=patient pressure/terminal pressure
$P_{char}$=characteristic pressure
$P_{sys}$=system pressure In this case, nasal pressure can be determined using equation (4) and $P_T$ along with a characteristic pressure $P_{char}$. Characteristic pressure relates to the pressure contribution of the system and is described and can be determined as per priority applications U.S. 62/036,769, U.S. 62/046,000 and PCT application published as WO2015/033288.

In an alternative variation to the first exemplary embodiment, in addition to measuring the pressure in, at or near/proximate the outlet of each outlet of the patient interface (e.g. each nasal prong) or in, at or proximate each nare of the patient. A third system pressure is measured in a portion of the flow therapy system (using a sensor e.g. in the nasal cannula manifold 25c, or delivery conduit 3c) that supplies gases flow to both nasal passages.

In this variation, the system pressure can be used to determine $Q_{offset}$ using equations (1)-(4). In this case, there is a characteristic pressure, which can be determined an utilised in the equations.

Figure 4:
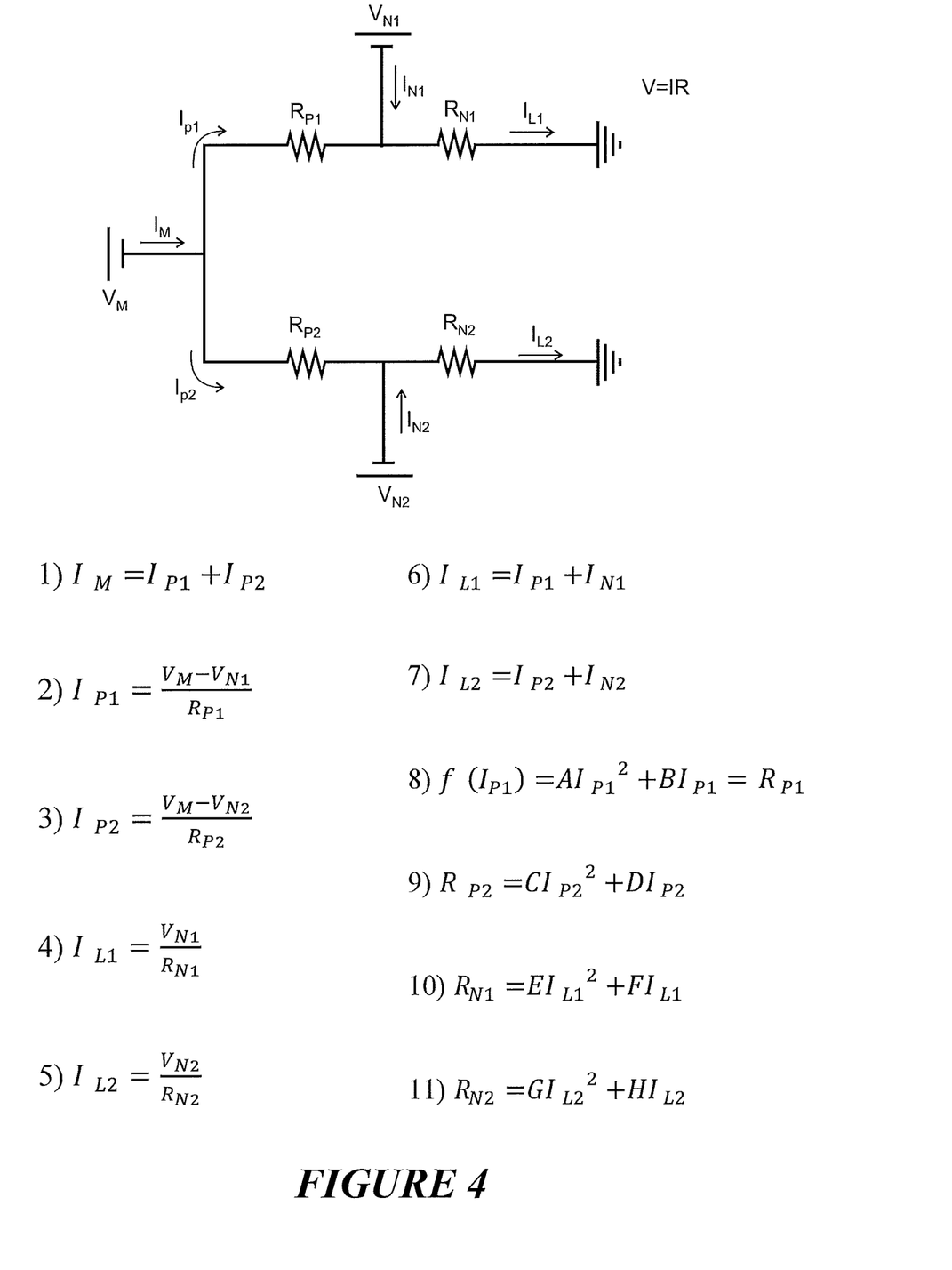
FIG. 4 illustrates an electrical analogy model of an embodiment.

In an alternative, but analogous approach to either variation above, the system (apparatus and patient) can be modelled as an electrical analogy as per FIG. 4. FIG. 4 shows an electrical analogy to model the system parameters in this variation. The electrical analogy below may be used to determine respiratory flow rate with two or more pressure sensors. Volts (V) is analogous to pressure, electrical resistance (R) is analogous to flow resistance, current (I) is analogous to flowrate, and earth is analogous to the atmosphere. The schematic represents flow directions analogous of expiration however the same principal also works for inspiration. Here the prong resistances ($R_{P1}$ and $R_{P2}$) and the nasal resistances ($R_{N1}$ and $R_{N2}$) are functions of prong flows ($I_{P1}$ and $I_{P2}$), and the leakage flows ($I_{L1}$ and $I_{L2}$), respectively. Preferably the relationship is a look up table, graph or mathematical function that relates patient pressure to the nasal flow rate from peak respiratory flow rate. The system can be modelled with the following equations:

$$I_M = I_{P1} + I_{P2}$$

$$I_{P1} = \frac{V_M - V_{N1}}{R_{P1}}$$

$$I_{P2} = \frac{V_M - V_{N2}}{R_{P2}}$$

$$I_{L1} = \frac{V_{N1}}{R_{N1}}$$

$$I_{L2} = \frac{V_{N2}}{R_{N2}}$$

$$I_{L1} = I_{P1} + I_{N1}$$

$$I_{L2} = I_{P2} + I_{N2}$$

$$f(I_{P1}) = AI_{P1}^2 + BI_{P1} = R_{P1}$$

$$R_{P2} = CI_{P2}^2 = DI_{P2}$$

$$R_{N1} = EI_{L1}^2 + FI_{L1}$$

$$R_{N2} = GI_{L2}^2 + HI_{L2}$$

Where:
$V_M$ is the voltage of the manifold, which corresponds to the pressure in the manifold or the system pressure ($P_{sys}$)

$V_{n1}$ and $V_{n2}$ are the nasal passage voltages for nasal passages 1 and 2, which correspond to the pressure of nasal passages 1 and 2.

$I_M$ is the manifold current, which corresponds to the flow rates for the manifold or the system flow rate.

$I_{n1}$ and $I_{n2}$ are the nasal passage current for nasal passage 1 and 2, which correspond to the respiratory demand flow rates for nasal passages 1 and 2.

$I_{P1}$ and $I_{P2}$ are the prong currents for prongs 1 and 2, which correspond to the flow rates for prongs 1 and 2.

$I_{L1}$ and $I_{L2}$ are the respective leakage currents, which correspond to the respective leakage (offset) flow rates.

$R_{P1}$ and $R_{P2}$ are the prong electrical resistances for prongs 1 and 2, which correspond to the flow rate resistances (resistances to flow) for prongs 1 and 2.

$R_{N1}$ and $R_{N2}$ are the respective leakage electrical resistances, which correspond to the respective leakage (offset) flow rate resistances (resistances to flow).

The required resistance (R), voltage (V) and current (I) parameters can be correlated to corresponding resistance to flow, pressure and flow rate values. The controller 13 can be configured to determine that the required parameters then solve the necessary equations to determine the offset flow rates, which can be solved to determine respiratory demand. The system of equations and solution to an electrical system such as this will be solvable to someone skilled in the art. The controller can be configured to use this electrical analogy and measured and empirically determined parameters to determine respiratory demand of each nasal passage and overall.

As an example, where nasal pressures are measured at each nasal passage, the equations can be used to solve for $I_{N1}$ and $I_{N2}$ which are respective inspiratory demand flow rates for respective nasal passages. $V_{N1}$, $V_{N2}$ are the respective nasal pressures as measured, and $R_{N1}$, $R_{N2}$ are equivalent to respective nasal resistances to flow, the values of which are obtained from empirically determined data. The inspiratory demand flows can be added to find the overall inspiratory demand. These equations could also be solved for expiratory demand and peak inspiratory/expiratory demand.

In the example above, the system pressure ($V_M$) and related parameters are not used. However, in a further variation, they could be used, where $V_M$ is the measured system pressure $P_{system}$. Measuring the system pressure and solving the model to determine $I_{P1}$, $I_{P2}$ (flow through each nasal prong) may help quantify any flow bias through either prong of the nasal cannula. For example, in an example cannula, more flow comes out the prong away from the tubing. Also, knowing the system pressure as well as each prong pressure could be useful for identifying changes in $R_{P1}$ and $R_{P1}$ (prong resistances) that may result from being deformed in shape to fit odd shaped nostrils. In short, it is useful if the flow is not evenly split between the two prongs due to cannula design or deformation of the soft prongs as this information can be used to determine if respiratory demand is met and/or the respiratory demand overall and in each nostril. Using $V_m$, $I_m$, $I_{P1}$, $I_{P2}$ $R_{P1}$, and/or $R_{P2}$, the total gas flow rate required to be supplied by the breathing apparatus and/or the gas flow rate to be required through each nasal prong to meet respiratory demand (overall and/or for each nasal passage), can be determined.

In a further variation, if for example a cannula is designed such that the flow is always split evenly between the two prongs and the prongs are such that they do not deform significantly to alter their resistance to flow ($R_{P1}$, $R_{P2}$) then $I_m$ (total manifold flow) could be measured with a flowmeter at the flow source and $R_{P1}$ and $R_{P2}$ retrieved from a lookup table, equation etc. In this case it could be assumed that $R_{P1} = R_{P2}$. Measuring Vm (i.e. manifold pressure before splitting into two prongs) allows us to measure $R_{P1}$ and $R_{P2}$ continuously and directly (more accurate).

Second Exemplary Embodiment for Determining Respiratory Demand Using a Relationship Between Nasal Pressure and Offset Flow In a second exemplary embodiment, sensors are used to measure the pressure of each nasal passage, but instead of using the equations above, an alternative method is utilised to determining offset flow, as described and US priority application 61/994,374 and PCT application published as WO2015/033288.

The patient pressure (that is, terminal pressure or nasal pressure) for each nasal passage as measured, step 30, indicates a relationship between the delivered gas flow rate and the respiratory demand for that nasal passage. The controller determines the overall respiratory demand and/or flow rate offset using both measured nasal pressures. The flow rate offset for each nostril can be determined, step 31*a*, from a look up table, mathematical relationship, graph or the like that correlates the offset flow rate to patient pressure.

Figure 5:
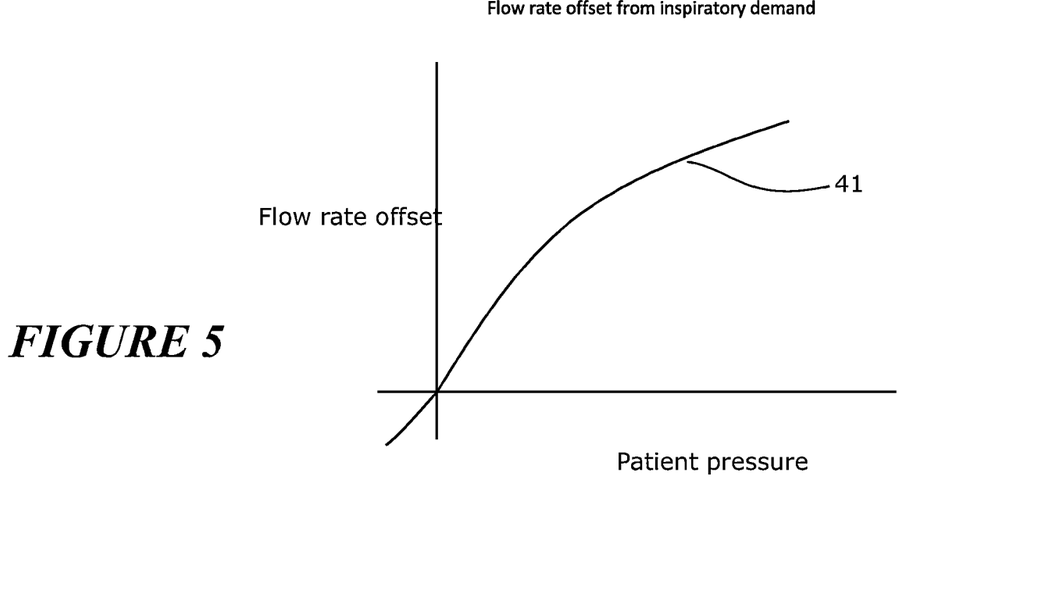
FIG. 5 illustrates a generic patient pressure versus flow rate offset curve.

As an example in relation to determining peak inspiratory demand, a generic relationship 41 showing flow rate offset from peak inspiratory demand versus terminal pressure is shown in FIG. 5. The relationship 41 can be calculated or determined empirically. An empirical derivation can be determined by taking a population average which is stored in the controller and accessed as required via a look-up table, calculation from the relationship equation or similar, or by creating a relationship for each individual patient as part of a calibration step/learning period. An individual patient relationship could be found by taking system pressure measurements over a range of flow rates allowing for a stabilisation period of say 5 breaths, or several minutes at each flow rate. This calibration could be performed at the onset of therapy and/or at intervals throughout the therapy and/or when initiated by the user or the device, for example when the patient has moved causing a change in the arrangement of the device tubing and thus its resistance to flow. The range of tested flow rates may be set by the device or may be chosen by the user based on the expected delivered flow rates throughout the patient's treatment.

Figure 6:
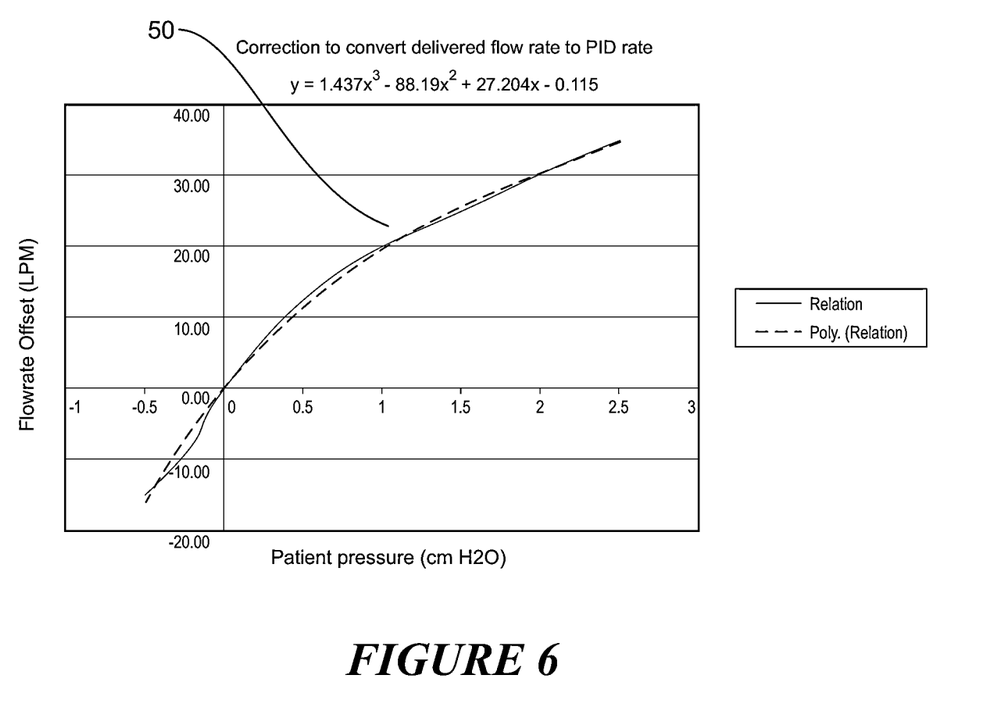
FIG. 6 illustrates a patient pressure versus flow rate offset curve.

The relationship 50 depicted by the graph in FIG. 6 shows the relationship between the patient pressure and flow rate offset (from the PID flow rate). If the offset flow rate is positive, this indicates that the gas flow rate being delivered is more than the peak inspiratory demand. If the offset flow rate is negative in that indicates that insufficient gas flow rate is being delivered to the patient and will not meet their peak inspiratory demand flow rate. Optionally, the actual PID flow rate can be calculated by subtracting the delivered gas flow rate from the offset flow rate.

Also, more generally in a variation of the second exemplary embodiment, the pressure parameter for each nasal passage might not be measured at the nasal passage itself, but rather at some point in the system prior to the nasal passage ($P_{system}$), system), like in the nasal prong, or other conduit dedicated to the nasal passage in question using a pressure sensor (e.g. 25c, 3c) positioned as required. This pressure is a system pressure. In this case a characteristic pressure of the system between the pressure measurement point and the nasal passage is used to determine the terminal pressure from the system pressure. In this case, the controller is configured to determine terminal pressure (for each nasal passage) from the measured system pressure (relating to each nasal passage) in accordance with the following equation (4).

$$P_T = P_{sys} - P_{char}$$

where
$P_T$=patient pressure/terminal pressure
$P_{char}$=characteristic pressure
$P_{sys}$=system pressure In this case, nasal pressure can be determined using equation (4) and $P_T$ along with a characteristic pressure $P_{char}$. Characteristic pressure relates to the pressure contribution of the system and is described and can be determined as per U.S. priority application 61/994,374 and PCT application published as WO2015/033288.

Further Embodiments

Figure 7:
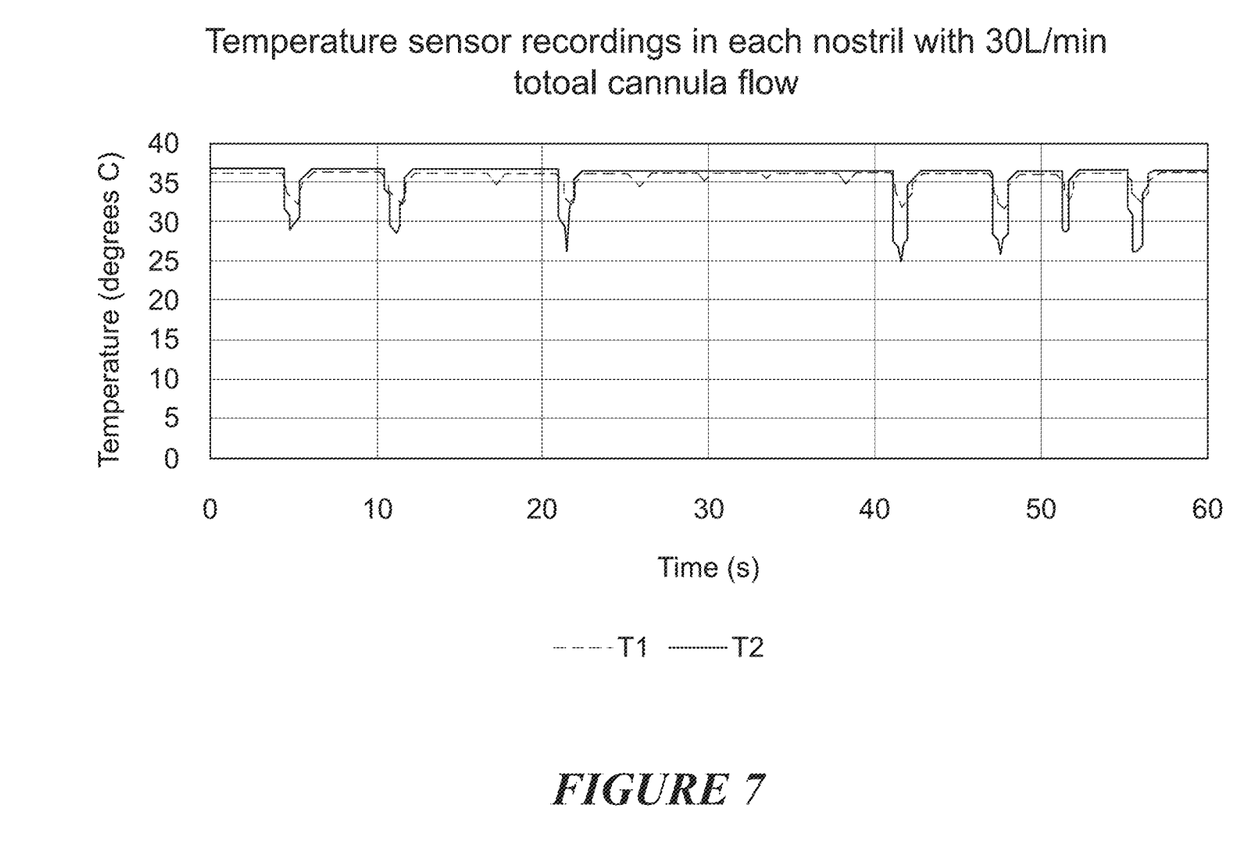
FIG. 7 illustrates using nasal temperature to determine compliance with respiratory demand.

In an alternative embodiment, nasal temperature can be measured for each nasal passage, step 30, and an indication of respiratory demand determined, step 32, for example as described in PCT application published as WO2015/033288. For example, and referring to FIG. 7, the temperature of $Q_{offset}$ is measured in each nostril individually. Here the total cannula flow is 30 L/min and the delivered temperature is approx. 37 degrees. When the temperature dips more than a threshold, for example 5 degrees below 30 L/min, the gas flow rate is clearly not meeting that particular breath's PID. In the 60 second recording there are 13 breaths. It can be seen that for some breaths PID is not met in both nostrils and for others PID is met. It is entirely possible that PID is met in one nostril and not the other. Breath 4 (just before 20 seconds) is borderline for such a case.

In an alternative embodiment, another nasal parameter can be measured for each nasal passage, step 31, and an indication of respiratory demand determined, step 32 for example as described in PCT application published as WO2015/033288.

Figure 8:
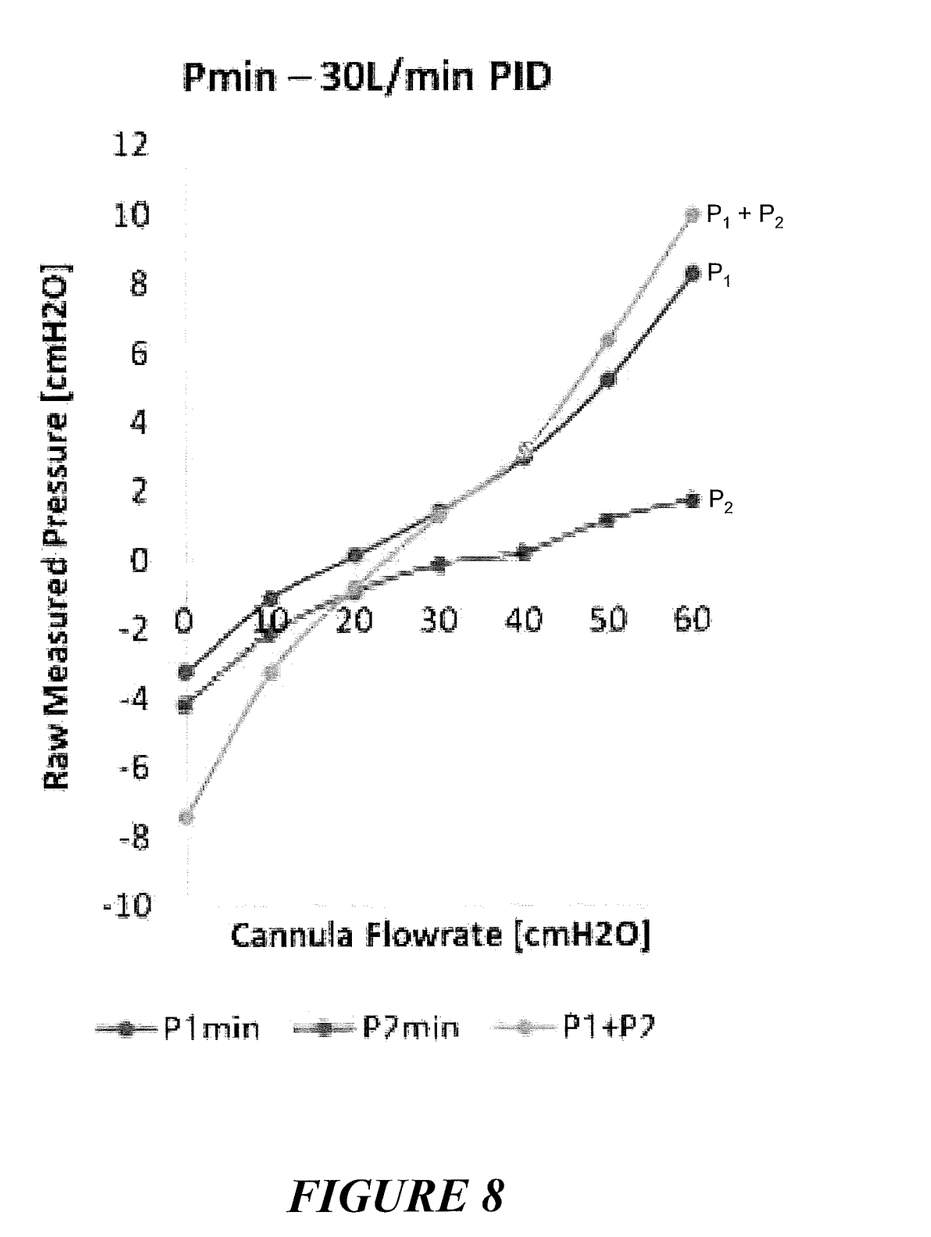
FIG. 8 illustrates cannula flow with respect to individual nasal and combined nasal pressures.

It is possible to determine whether an apparatus estimating respiratory demand (e.g. peak inspiratory demand) uses information from two nostrils or uses information that does not differentiate between nostrils. For example, and referring to FIG. 8, one way is to obtain a PID demand estimate in a controlled experiment where PID is controlled and known e.g. an anatomical airway and face model connected to a lung simulator. Then maintain the same PID with the lung simulator and partially occlude one nostril. If the PID estimate deviates by less than a threshold, e.g. 5 L/min, then the device is likely to use information from both nostrils. In this case the total PID is likely to be taken from the larger of the two nostrils individual PIDs. Where individual nostrils are not differentiated the total PID is likely to be a combination of each nostril's PID and suffer from an underestimated PID bias.

The invention claimed is:

1. A method of estimating a respiratory demand of a patient being administered flow therapy comprising:
   using a controller of a flow therapy apparatus:
   controlling a flow generator of a flow therapy apparatus so that the flow generator administers gas to the patient through both nostrils using a non-sealing patient interface, wherein the gas administered to the patient is at a predetermined gas flow rate;
   for each nostril, measuring a nostril parameter associated with that nostril using one or more sensors of the flow therapy apparatus, the nostril parameter being one or more of:
     a respiratory demand of that nostril,
     a parameter indicative of the respiratory demand of that nostril, or
     a parameter from which the respiratory demand of that nostril is configured to be derived;
     wherein the nostril parameter associated with each nostril is a pressure of a nasal passage for that nostril, or a pressure of a conduit leading to the nasal passage of that nostril, or both; and
   calculating the respiratory demand of the patient from the nostril parameter associated with each nostril using a relationship between the nostril parameter associated with each nostril and the respiratory demand of the patient, wherein the respiratory demand of the patient is the gas flow rate required by the patient during breathing,
   wherein the respiratory demand is calculated by:
     combining the pressure of the nasal passage for each nostril, and using the relationship to determine an offset flow rate or a respiratory demand flow rate for the patient using the combined pressure of the nasal passage for each nostril, the relationship being stored in the controller, or
     using the relationship, determining an offset flow rate or a respiratory demand flow rate for each nostril using the pressure of the nasal passage for each nostril and combining the offset flow rate or nasal respiratory demand flow rate for each nostril to provide the offset flow rate or respiratory demand flow rate for the patient.

2. A method according to claim 1 wherein the respiratory demand of the patient is:
an inspiratory demand, and/or
an expiratory demand.

3. A method according to claim 1 wherein the relationship is one or more of:
a look up table,
a mathematical relationship, or
a graph,
wherein the relationship correlates the offset flow rate or respiratory demand to the pressure of the nasal passage for each nostril or for the patient.

4. A method according to claim 3 wherein the relationship comprises the mathematical relationship that is:

$$Q_{offset} = SQR\left(\frac{ABS(P_T)}{R_{nasal}}\right)$$

wherein
$Q_{offset}$ is the offset flow rate for the respective nasal passage at a point in time and is calculated using said mathematical relationship,
$P_T$ is a terminal pressure in, at, near, or proximate an outlet of a respective nasal prong of the non-sealing patient interface or in, at, near, or proximate the respective nasal passage of the patient—at a point in time, and
$R_{nasal}$ is a nasal resistance to flow of the respective nasal passage.

5. A method according to claim 4 wherein:
for a non-laminar flow condition, the mathematical relationship is determined using the following equation:

$$R_{nasal} = \frac{P_{trans} - P_{char}}{Q_{offset}^2}$$

wherein
$P_{trans}$ is a pressure at an inspiration/expiration transition of breathing,
$P_{char}$ is a system characteristic pressure when $P_{trans}$ is being measured, wherein $P_{char}$ is zero or close to zero when measured at the nasal passage or nasal prongs,
and wherein for a laminar flow condition, the mathematical relationship is determined using the following equation:

$$R_{nasal} = \frac{P_{trans} - P_{char}}{Q_{offset}}$$

wherein $P_{char}=0$ if the nostril parameter associated with each nostril is the pressure of the nasal passage for that nostril.

6. A method according to claim 3 wherein the mathematical relationship is formed from an electrical analogy of the patient and is:

$$I = V/R$$

wherein
I is a current in the electrical analogy and corresponds to the offset flow rate for each nostril or the patient,
V is voltage in the electrical analogy and corresponds to the pressure of the nasal passage for each nostril, and
R is a resistance in the electrical analogy and corresponds to a nasal resistance to flow.

7. A method according to claim 1 wherein:
a gas flow rate required to be supplied through both nostrils, or
a gas flow rate to be required through each nasal prong of the non-sealing patient interface to meet a respiratory demand of each nasal passage or of the patient, is configured to be determined using one or more of the following equations:

$$I_M = I_{P1} + I_{P2}$$

$$I_{P1} = \frac{V_M - V_{N1}}{R_{P1}}$$

$$I_{P2} = \frac{V_M - V_{N2}}{R_{P2}}$$

$$I_{L1} = \frac{V_{N1}}{R_{N1}}$$

$$I_{L2} = \frac{V_{N2}}{R_{N2}}$$

$$I_{L1} = I_{P1} + I_{N1}$$

$$I_{L2} = I_{P2} + I_{N2}$$

$$f(I_{P1}) = AI_{P1}^2 + BI_{P1} = R_{P1}$$

$$R_{P2} = CI_{P2}^2 = DI_{P2}$$

$$R_{N1} = EI_{L1}^2 + FI_{L1}$$

$$R_{N2} = GI_{L2}^2 + HI_{L2}$$

wherein
$V_M$ is a voltage of a manifold of the non-sealing patient interface, which corresponds to a pressure in the manifold or a system pressure ($P_{sys}$),
$V_{n1}$ and $V_{n2}$ are nasal passage voltages for first and second nasal passages, which correspond to a pressure of the first and second nasal passages,
$I_M$ is a manifold current, which corresponds to a flow rate in the manifold or a system flow rate,
$I_{n1}$ and $I_{n2}$ are nasal passage current for the first and second nasal passages, which correspond to the respiratory demand flow rates for the first and second nasal passages,
$I_{P1}$ and $I_{P2}$ are prong currents for the first and second nasal passages, which correspond to the flow rates for the first and second nasal passages,
$I_{L1}$ and $I_{L2}$ are respective leakage currents, which correspond to the respective offset flow rates for the first and second nasal passages,
$R_{P1}$ and $R_{P2}$ are prong electrical resistances for the first and second nasal passages, which correspond to resistances to flow for the first and second nasal passages, and
$R_{N1}$ and $R_{N2}$ are respective leakage electrical resistances, which correspond to the respective offset resistances to flow for the first and second nasal passages.

8. A method according to claim 1 further comprising displaying on a display the respiratory demand of the patient determined from the nostril parameter associated with each nostril.

9. A method according to claim 1 further comprising manually or automatically controlling the flow therapy based on the respiratory demand of the patient determined from the nostril parameter associated with each nostril.

10. A flow therapy system comprising:
a non-sealing patient interface, and
a flow therapy apparatus comprising:
   a flow generator,
   one or more sensors, and
   a controller configured to:
      control the flow generator to administer gas at a gas flow rate to the patient through both nostrils using the non-sealing patient interface,
      for each nostril, measure from the one or more sensors a nostril parameter associated with that nostril, the nostril parameter being one or more of:
         a respiratory demand of that nostril,
         a parameter indicative of the respiratory demand of that nostril, or
         a parameter from which the respiratory demand of that nostril is configured to be derived,
         wherein the nostril parameter associated with each nostril is a pressure of a nasal passage for that nostril, or a pressure of a conduit leading to the nasal passage of that nostril, or both;
      calculate a respiratory demand of the patient from the nostril parameter associated with each nostril using a relationship between the nostril parameter associated with each nostril and the respiratory demand of the patient, wherein the respiratory demand of the patient is the gas flow rate required by the patient during breathing,
      wherein the respiratory demand is calculated by:
         combining the pressure of the nasal passage for each nostril, and using the relationship to determine an offset flow rate or a respiratory demand flow rate for the patient using the combined pressure of the nasal passage for each nostril, or
         using the relationship, determining an offset flow rate or a respiratory demand flow rate for each nostril using the pressure of the nasal passage for each nostril and combining the offset flow rate or nasal respiratory demand flow rate for each nostril to provide the offset flow rate or respiratory demand flow rate for the patient.

11. A system according to claim 10 wherein the respiratory demand of the patient is:
an inspiratory demand, and/or
an expiratory demand.

12. A system according to claim 10 wherein the relationship is one or more of:
a look up table,
a mathematical relationship, or
a graph,
wherein the relationship correlates the offset flow rate to the pressure of the nasal passage for each nostril or for the patient.

13. A system according to claim 12 wherein the relationship comprises the mathematical relationship that is:

$$Q_{offset} = SQR\left(\frac{\text{ABS}(P_T)}{R_{nasal}}\right)$$

wherein
$Q_{offset}$ is the offset flow rate for the respective nasal passage at a point in time and is calculated using said mathematical relationship,
$P_T$ is a terminal pressure in, at, near, or proximate an outlet of a respective nasal prong of the non-sealing patient interface or in, at, near, or proximate the respective nasal passage of the patient—at a point in time, and
$R_{nasal}$ is a nasal resistance to flow of the respective nasal passage.

14. A system according to claim 13 wherein:
for a non-laminar flow condition, the mathematical relationship is determined using the following equation:

$$R_{nasal} = \frac{P_{trans} - P_{char}}{Q_{offset}^2}$$

wherein
$P_{trans}$ is a pressure at an inspiration/expiration transition of breathing,
$P_{char}$ is a system characteristic pressure when $P_{trans}$ is being measured,
wherein $P_{char}$ is zero or close to zero when measured at the nasal passage or nasal prongs,
and wherein for a laminar flow condition, the mathematical relationship is determined using the following equation:

$$R_{nasal} = \frac{P_{trans} - P_{char}}{Q_{offset}}$$

wherein $P_{char}=0$ if the nostril parameter associated with each nostril is the pressure of the nasal passage for that nostril.

15. A system according to claim 12 wherein the relationship comprises the mathematical relationship that is formed from an electrical analogy of the patient and is:

$I=V/R$ wherein
I is a current in the electrical analogy and corresponds to the offset flow rate for each nostril or the patient,
V is voltage in the electrical analogy and corresponds to the pressure of the nasal passage for each nostril, and
R is a resistance in the electrical analogy and corresponds to a nasal resistance to flow.

16. A system according to claim 10 wherein:
a gas flow rate required to be supplied through both nostrils, or
a gas flow rate to be required through each nasal prong of the non-sealing patient interface to meet a respiratory demand of each nasal passage or of the patient, is configured to be determined using one or more of the following equations:

$$I_M = I_{P1} + I_{P2}$$

$$I_{P1} = \frac{V_M - V_{N1}}{R_{P1}}$$

$$I_{P2} = \frac{V_M - V_{N2}}{R_{P2}}$$

-continued $$I_{L1} = \frac{V_{N1}}{R_{N1}}$$

$$I_{L2} = \frac{V_{N2}}{R_{N2}}$$

$$I_{L1} = I_{P1} + I_{N1}$$

$$I_{L2} = I_{P2} + I_{N2}$$

$$f(I_{P1}) = AI_{P1}^2 + BI_{P1} = R_{P1}$$

$$R_{P2} = CI_{P2}^2 + DI_{P2}$$

$$R_{N1} = EI_{L1}^2 + FI_{L1}$$

$$R_{N2} = GI_{L2}^2 + HI_{L2}$$

wherein $V_M$ is a voltage of a manifold of the non-sealing patient interface, which corresponds to a pressure in the manifold or a system pressure ($P_{sys}$), $V_{n1}$ and are nasal passage voltages for first and second nasal passages, which correspond to a pressure of the first and second nasal passages, $I_M$ a manifold current, which corresponds to a flow rate in the manifold or a system flow rate, $I_{n1}$ and $I_{n2}$ are nasal passage current for the first and second nasal passages, which correspond to the respiratory demand flow rates for the first and second nasal passages, $I_{P1}$ and $I_{P2}$ are prong currents for the first and second nasal passages, which correspond to the flow rates for the first and second nasal passages, $I_{L1}$ and $I_{L2}$ are respective leakage currents, which correspond to the respective offset flow rates for the first and second nasal passages, $R_{P1}$ and $R_{P2}$ are prong electrical resistances for the first and second nasal passages, which correspond to resistances to flow for the first and second nasal passages, and $R_{N1}$ and $R_{N2}$ are respective leakage electrical resistances, which correspond to the respective offset resistances to flow for the first and second nasal passages.

17. A system according to claim 10 further comprising the controller being configured to display on a display of the apparatus the respiratory demand of the patient determined from the nostril parameter associated with each nostril.

18. A system according to claim 10 further comprising the controller controlling flow therapy based on the respiratory demand of the patient determined from the nostril parameter associated with each nostril.

19. A respiratory support system comprising:
a non-sealing patient interface, and
a respiratory support apparatus comprising:
 a flow generator,
 one or more sensors, and
 a controller configured to:
  control the flow generator to administer gas at a gas flow rate to the patient through both nostrils using the non-sealing patient interface,
  for each nostril, measure from the one or more sensors a nostril parameter associated with that nostril, the nostril parameter being one or more of:
   a respiratory demand of that nostril,
   a parameter indicative of the respiratory demand of that nostril, or
   a parameter from which the respiratory demand of that nostril is configured to be derived,
   wherein the nostril parameter associated with each nostril is a pressure of a nasal passage for that nostril, or a pressure of a conduit leading to the nasal passage of that nostril, or both;
  calculate a respiratory demand of the patient from the nostril parameter associated with each nostril using a relationship between the nostril parameter associated with each nostril and the respiratory demand of the patient, wherein the respiratory demand of the patient is the gas flow rate required by the patient during breathing,
  wherein the respiratory demand is calculated by:
   combining the pressure of the nasal passage for each nostril, and using the relationship to determine an offset flow rate or a respiratory demand flow rate for the patient using the combined pressure of the nasal passage for each nostril, the relationship being stored in the controller, or
   using the relationship, determining an offset flow rate or a respiratory demand flow rate for each nostril using the pressure of the nasal passage for each nostril and combining the offset flow rate or nasal respiratory demand flow rate for each nostril to provide the offset flow rate or respiratory demand flow rate for the patient.

* * * * *